United States Patent [19]

Dunlop

[11] 4,399,701
[45] Aug. 23, 1983

[54] METHOD AND MEANS FOR DETECTING DECAY IN WOOD

[75] Inventor: John I. Dunlop, Centennial Park, Australia

[73] Assignee: Unisearch Limited, Kensington, Australia

[21] Appl. No.: 268,181

[22] Filed: May 29, 1981

[30] Foreign Application Priority Data

Jun. 3, 1980 [AU] Australia ............................. PE3858

[51] Int. Cl.³ ...................... G01N 29/00; G01N 24/00
[52] U.S. Cl. ........................................ 73/579; 73/630
[58] Field of Search .................. 73/579, 630, 594, 580

[56] References Cited

U.S. PATENT DOCUMENTS

| | | | |
|---|---|---|---|
| 3,023,609 | 3/1962 | Schubring | 73/579 |
| 3,043,132 | 7/1962 | Schubring | 73/579 |
| 3,345,861 | 10/1967 | Heath | 73/579 |
| 3,521,483 | 7/1970 | Miller et al. | 73/598 |
| 3,531,983 | 10/1970 | Heath et al. | 73/579 |
| 3,877,294 | 4/1975 | Shaw | 73/579 |
| 4,297,872 | 11/1981 | Ikeda et al. | 73/579 |

FOREIGN PATENT DOCUMENTS 1302028  1/1973  United Kingdom ................. 73/579

OTHER PUBLICATIONS

Vibration Analysis of Thin-Walled Cylindrical Shells, by Koval, in MB Vibration Notebook, Jan. 1962, vol. 8, No. 1, © by Textron Elec. MB.
Sweep Rondom Vibration, by Booth in MB Vibration Notebook, Feb. 1963, vol. 9, No. 1 © by Textron Elec.

*Primary Examiner*—Stephen A. Kreitman
*Assistant Examiner*—David V. Carlson

[57] ABSTRACT

A method and apparatus for detecting degradation in wood by applying acoustic waves along the wood grain and measuring the bandwidths and frequencies or standing wave resonances induced in the wood as the frequency of the applied waves is varied. Good quality wood exhibits a substantially harmonic relationship between the frequencies at which resonances occur and the bandwidths of the resonances are relatively small.

8 Claims, 1 Drawing Figure

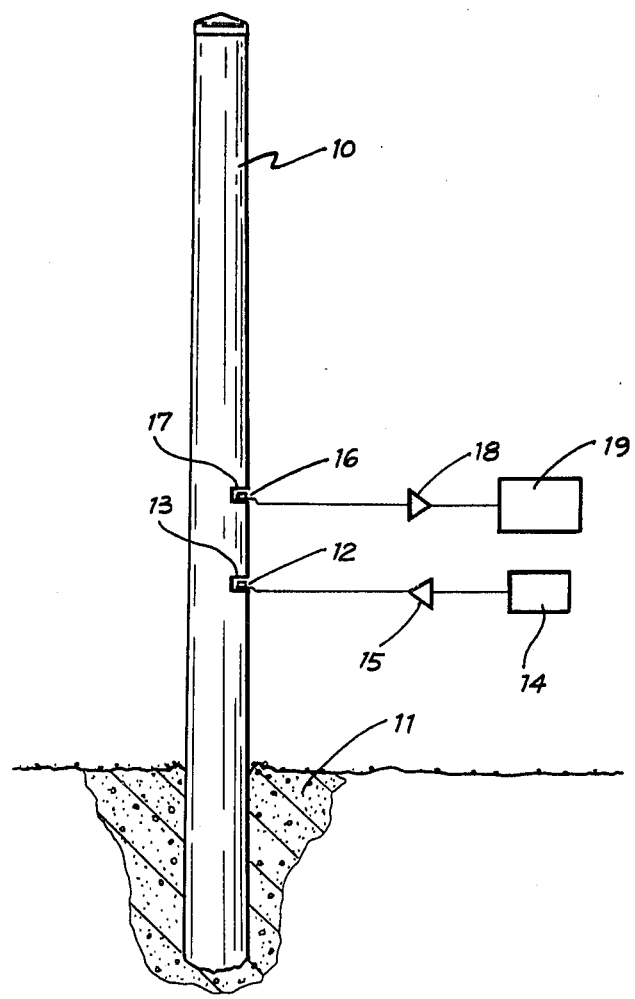

METHOD AND MEANS FOR DETECTING DECAY IN WOOD

The present invention relates to a method and means for detecting degradation in wood by means of acoustic waves.

Widespread use has been made of the measurement of acoustic velocity for detecting decay and degradation in wood articles. Attenuation of acoustic pulses has also been described in relation to measuring the strength of lumber, but there has been no recognition of how to employ the attenuation or absorption of acoustic waves for detecting degradation in wood articles. It is most desirable that there be a rapid and easy means by which degradation in timber can be detected particularly in applications where wood utility poles are in situ or before their installation. Suitability for detecting deterioration of wood pier pilings and degradation in laminated timber beams is also envisaged.

It is, therefore, one object of the present invention to provide a method and means for readily detecting degradation in wood articles.

In one form the present invention provides a method of detecting deterioration in wood articles by applying acoustic waves along the wood grain and measuring the band widths and frequencies of the acoustic or standing wave resonances in said articles as the frequency of said waves is varied over a predetermined range.

The absence of degradation in the interior will be represented by relatively narrow bandwidths of the acoustic resonances and by the presence of a harmonic relationship between the frequencies of the said resonances. The presence of degradation will be characterised by either board bandwidths of the resonances or anharmonicity of the frequencies at which the resonances occur.

In another form the present invention provides means for detecting deterioration in wood articles comprising means for applying longitudinal acoustic waves to a wood article over a predetermined range of frequencies and means for detecting and recording the standing wave frequencies and resonance bandwidths.

The present invention is particularly suited for determining the presence of rot or decay in poles in situ or ones ready for use and from the foregoing it will be seen that this can be achieved by measurement of the damping of longitudinal acoustic waves in a pole by measurement of standing wave frequencies and resonanic band widths.

The present invention will now be described by way of example with reference to the accompanying drawing which is a schematic representation of apparatus in accordance with the invention when in use.

The drawing FIGURE schematically represents a wooden pole or pier 10 embedded in the ground /1. For this embodiment an acoustic transducer 12 is inserted into a slot 13 and coupled to the bottom of the slot via grease. Transducer 12 is driven by a variable frequency voltage generator 14 through amplifier 15. A further transducer 16 is located in slot 17 in similar manner to transducer 13. Transducer 16 is coupled via amplifier 18 to voltage recording means such as voltmeter 19.

These transducers may be attached to either the same or opposite ends of say a horizontal pole or to the top of a standing pole. Further the transducer arrangement may be such that driving and detecting may be carried out using a single transducer.

Two types of transducers have been found to produce particularly reliable results and they are piezoelectric bender disc transducers and rectangular bimorphic piezo electric strip transducers. The transducers 12, 16 are preferably applied under pressure to a cross-section of pole 10 perpendicular to the grain of the timber with coupling grease between transducer 12, 16 and surface of slots 13, 17 respectively. Slots 13, 17 are cut into pole 10 to expose cross sections perpendicular to the grain of the timber and wherein transducers 12, 16 are each applied to the bottom face of their respective slots.

In operation the frequency of the driving voltage applied to transducer 13 is varied over, say, a range that includes the frequencies of the first twenty standing wave harmonics and the voltage from detecting transducer 16 is recorded.

The quality of the pole 10 under test will be shown to be good by the presence of a substantially harmonic relationship between the frequencies at which resonances occur i.e. these frequencies are substantially multiple whole numbers of a fundamental frequency that depends on the length of the pole and the velocity of compression acoustic waves in wood. Also the width of these resonances along the frequency scale are small, usually of the rder of 50 Hz at the half power points i.e. at $1/\sqrt{2}$ of the maximum height.

Poles containing rot r other forms of deterioration are characterized by either board bandwidths of the resonances or resonant frequencies which do not bear a substantially harmonic relationship to one another.

I claim:

1. A method of detecting degradation in wood articles comprising the steps of applying acoustic waves along the wood grain, and measuring the band widths and frequencies of the acoustic or standing wave resonances in said articles as the frequency of said waves is varied over a predetermined range.

2. A method as claimed in claim 1 wherein the acoustic waves are applied via a transducer.

3. Means for detecting degradation in wood articles comprising means for applying longitudinal acoustic waves to a wood article along the wood grain over a predetermined range of frequencies and means for detecting and recording the standing wave frequencies and resonance bandwidths associated therewith.

4. Means for detecting degradation as claimed in claim 3, wherein the means for applying acoustic waves and the means for detecting are transducers.

5. Means for detecting degradation as claimed in claim 4, wherein said transducers are piezo electric bender disc transducers.

6. Means for detecting degradation as claimed in claim 4, wherein said transducers are rectangular bimorphic piezo-electric strip transducers.

7. Means for detecting degradation as claimed in claim 4, wherein the acoustic wave applying transducer is driven by a variable frequency voltage generator.

8. Means for detecting degradation as claimed in claim 4, wherein the detecting transducer is connected to voltage recording means.

* * * * *